(12) United States Patent
Kubota et al.

(10) Patent No.: US 7,824,911 B2
(45) Date of Patent: Nov. 2, 2010

(54) HEPATIC STELLATE CELL PROGENITORS AND METHODS OF ISOLATING SAME

(75) Inventors: Hiroshi Kubota, Aomori (JP); Lola M. Reid, Chapel Hill, NC (US)

(73) Assignee: University of North Carolina at Chapel Hill, Chapel Hill, NC (US)

(*) Notice: Subject to any disclaimer, the term of this patent is extended or adjusted under 35 U.S.C. 154(b) by 56 days.

(21) Appl. No.: 11/753,326

(22) Filed: May 24, 2007

(65) Prior Publication Data

US 2008/0009057 A1 Jan. 10, 2008

Related U.S. Application Data

(60) Provisional application No. 60/808,548, filed on May 26, 2006.

(51) Int. Cl.
*C12N 5/00* (2006.01)
(52) U.S. Cl. .................. 435/325; 435/378; 435/370
(58) Field of Classification Search .................. None
See application file for complete search history.

(56) References Cited

U.S. PATENT DOCUMENTS

| | | | |
|---|---|---|---|
| 6,069,005 A | 5/2000 | Reid et al. | |
| 2002/0182188 A1 | 12/2002 | Reid et al. | |
| 2003/0032182 A1 | 2/2003 | Kubota et al. | |
| 2004/0018621 A1 | 1/2004 | Reid et al. | |

OTHER PUBLICATIONS

Kmiec, Z. "Cooperation of Liver Cells in Health and Disease: Hepatic Stellate Cells" Advances in anatomy, embryology, and cell bio. (2001) vol. 161, pp. 29-39.*
Knittel et al, "Rat Liver Myofibroblasts and Hepatic Stellate Cells: Different Cell Populations of the Fibroblast Lineage With Fibrogenic Potential" Gastroenterology, 1999, vol. 117, pp. 1205-1221.*
Kubota et al, "Clonogenic hepatoblasts, common precursors for hepatocytic and biliary lineages, are lacking classical major histocompatibility complex class I antigen" Proceedings of the National Academy of Sciences, Oct. 24, 2000. vol. 97, No. 22, pp. 12132-12137.*
Nitou et al, "Immunohistochemical analysis of development of desmin-positive hepatic stellate cells in mouse liver" Journal of Anatomy, 2000, vol. 197, pp. 635-646.*
Zhou et al, "Engagement of (alpha)v (beta)3 Integrin Regulates Proliferation and Apoptosis of Hepatic Stellate Cells" The Journal of Biological Chemistry, Jun. 4, 2004, vol. 279, No. 23, pp. 23996-24006.*
Supplementary European Search Report corresponding to EP Application No. 07797729, dated Nov. 8, 2009; 7 pages.
Suskind, D. et at: "Searching for common stemcells of the hepatic and hematopoietic systems in the human fetal liver: CD34<+> cytokeratin ⅞<+> cells express markers for stellate cells" Journal of Hepatology 200402 NL, vol. 40, No. 2, Feb. 2004, pp. 261-268.
Higashi, N. et al: "Vitamin A storage in hepatic stellate cells in the regenerating rat liver: With special reference to zonal heterogeneity" Anatomical Record—Part A Discoveries in Molecular, Cellular, and Evolutionary Biology 200510 US, vol. 286, No. 2, Oct. 2005, pp. 899-907.
Sicklick, Jason K. et al: "Overlapping expression profile for hepatic epithelial progenitors and hepatic stellate cells" Gastroenterology, vol. 130, No. 4, Suppl. 2, Apr. 2006, p. A834, 2 pages.
Ogawa, T. et al: "Identification of vitamin A-free cells in a stellate cell-enriched fraction of normal rat liver as myofibroblasts" Histochemistry and Cell Biology 200702 DE, vol. 127, No. 2, Feb. 2007, pp. 161-174.
Kordes, C. et al: "CD133<+> hepatic stellate cells are progenitor cells"Biochemical and Biophysical Research Communications 20070112 US, vol. 352, No. 2, Jan. 12, 2007, pp. 410-417.
Kubota, H. et al: "Identification and characterization of vitamin A-storing cells in fetal liver: Implications for functional importance of hepatic stellate cells in liver development and hematopoiesis" Stem Cells 200709 US, vol. 25, No. 9, Sep. 2007, pp. 2339-2349.
International Search Report corresponding to PCT/US07/069645, dated Jul. 14, 2008, 1 page.
Friedman, S.L. "The Cellular Basis of Hepatic Firbosis- Mechanisms and Treatment Strategies," The New England Journal of Medicine, Jun. 1993, vol. 238, No. 25, pp. 1828-1835.
Geerts et al "Formation of Normla Desmin Intermediate Filaments in Mouse Hepatic Stellate Cells Requires Vimentin" Hepatology, 2001, vol. 33, pp. 177-188.
Sato et ai, "Hepatic Stellate Cells: Unique Characteristics in Cell Biology and Phenotype" Cell Structure and Function, 2003, vol. 28, pp. 105-112.
Winau et ai, "Ito Cells are Liver-Resident Antigen-Presenting Cells for Activating T Cell Responses" Immunity, Jan. 2007, vol. 26, pp. 117-129.

* cited by examiner

*Primary Examiner*—Allison M Ford
(74) *Attorney, Agent, or Firm*—Gilberto M. Villacorta; Sunit Talapatra; Foley & Lardner LLP

(57) ABSTRACT

The present invention relates to precursor cells to hepatic stellate cells, compositions comprising same and methods of isolating same. The surface antigenic profile of the precursors is MHC class Ia negative, ICAM-1$^+$, VCAM-1$^+$, β3-integrin$^+$. In addition to expression of these surface markers, the cells also express the intracellular markers desmin, vimentin, smooth muscle α-actin, nestin, hepatocyte growth factor, stromal derived factor-1α and H1x homeobox transcriptional factor.

12 Claims, 8 Drawing Sheets

SEQUENCE LISTING

<160> NUMBER OF SEQ ID NOS: 24

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atgagccagg cctactcgtc c                                               21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cagcacttca tgttgttgct g                                               21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tggaacagag attggaaggc c                                               21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
caggagtctc aagggtatta g                                               21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tccaaccgga gctatgtgac c                                               21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

-continued ctcaggttca gggaagaaaa g                                    21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atgtgtgaag aggaagacag c                                    21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtggtttcgt ggatgcccgc                                      20

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
atgaagtggg taacctttct cc                                   22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgtgatgtgt ttaggctaag gc                                   22

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggggaaaacc acaatttcca cac                                  23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

-continued ccaggaagga tcaacatctt tgc                                          23

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atggacgcca aggtcgtcgc                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gaaagggtct ctgagcacag                                              20

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tggacaagat tgttatcgtg g                                            21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
acgatttggg atggcacatc c                                            21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cctcggtcca gtctataaac c                                            21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cagccgttct gagggcgaag c                                            21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gatgaaaaaa ttggctggag g                                           21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gcaggtggca ttgaaggaca g                                           21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ctcaatgacc gctttgctag c                                           21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
accacgatgt tcctcttgag g                                           21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
atggatgacg atatcgctgc g                                           21

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gggtgtaaaa cgcagctcag taa                                         23

HEPATIC STELLATE CELL PROGENITORS AND METHODS OF ISOLATING SAME

CROSS-REFERENCE TO RELATED APPLICATIONS

This application claims priority to U.S. Provisional Application No. 60/808,548, filed May 26, 2006, the disclosure of which is incorporated herein by reference in its entirety.

FIELD OF THE INVENTION

The present invention relates generally to precursors of cells that comprise a mature liver. More particularly, the present invention relates to precursor cells to hepatic stellate cells, compositions comprising same and methods of isolating same.

BACKGROUND OF THE INVENTION

Hepatic stellate cells (HpStCs) were first described by Kupffer in the 19th century and were designated as "Sternellen" for their "stellar" sparkle when viewed under a microscope. HpStCs are liver-specific mesenchymal cells found in the Space of Disse and are comprised, in significant part, of cytoplasmic lipid droplets containing vitamin A. In fact, the lipid droplets contribute to the "sparkle" quality associated with HpStCs.

It is now accepted that HpStCs play a major role in the uptake, storage and release of vitamin A compounds, which are necessary particularly for vision, reproduction, and embryonic development. In mammals, about 50 to 80% of the total body vitamin A is normally stored in HpStCs.

HpStCs also play a central role in the production of growth factors, extracellular matrix components (ECMs), and matrix metalloproteinases in liver. A number of reports demonstrate that HpStCs secrete several mitogens for hepatocytes—such as EGF, TGFα and HGF—and play a central role in liver development and regeneration. Similarly, a numbers of studies demonstrate that an imbalance in ECM regulation is a factor in liver fibrosis or cirrhosis. Furthermore, the contractile properties of HpStCs suggest that they have a similar function to the pericytes, which control local blood flow in blood vessels. Taken together, these diverse functions of HpStCs illustrate their significant role in healthy and dysfunctional hepatic function.

Despite our growing understanding of the importance of HpStCs, the origin of HpStCs remains unknown. In early liver development, endodermal cells in the foregut give rise to hepatic diverticulum, which, in turn, develops into surrounding mesoderm called the septum transversum and forming the hepatic cords. While some have presumed that HpStC progenitors could derive from mesenchymal cells in the septum transversum, no HpStCs have been isolated from it, and surface markers enabling immunoselection and/or characterizing precursor HpStCs have yet to be identified.

Accordingly, there is a need for markers that specifically identify precursors to HpStCs and for a method of isolating same with said markers. In addition, there is a need for a method of propagating HpStC precursor cells in vitro.

SUMMARY OF THE INVENTION

In one embodiment of the present invention, a method of obtaining a population of cells enriched in hepatic stellate cell progenitor cells is provided comprising (a) providing a single cell suspension of cells from mammalian tissue; and sequentially, in any order, or substantially simultaneously, (b) removing from the single cell suspension those cells that express MHC class Ia antigen; and (c) isolating from the cell suspension those cells that are positive for Vitamin A fluorescence, to obtain a population of cells enriched in hepatic stellate cell progenitors. The mammalian tissue may be liver, pancreas, gut, lung, or bone marrow cells, preferably liver. The method may further comprise isolating from the cell suspension those cells that are positive for VCAM and/or β3-integrin; removing from the cell suspension those cells that express CD45; and/or isolating from the cell suspension those cells that express desmin, nestin, vimentin, smooth muscle alpha-actin or a combination thereof.

In some embodiments, the isolating and removing steps are carried out in a flow cytometer. Removal of cells that express MHC class I antigens may be carried out with a species-specific antibody against cells expressing those antigens; for example, utilizing antibodies against RT1A in rat liver cells. As well, the hepatic stellate progenitor cells may be human hepatic stellate cell progenitors.

In yet another aspect of the present invention, a method of obtaining a population of cells enriched in isolated hepatic stellate cell progenitors is provided comprising (a) obtaining a cell suspension of hepatic cells; and (b) sequentially, in any order, or substantially simultaneously, (i) isolating from the single cell suspension of liver cells those cells that are positive for ICAM-1 antigen (ii) removing those cells that are positive for MHC class I antigen, and (iii) isolating those cells that are positive for Vitamin A fluorescence as measured in a flow cytometer, to obtain a population of cells enriched in progenitors. The method may further comprise removing from the cell suspension those cells that express MHC class I antigen, CD45 or both and/or isolating from the cell suspension those cells that express desmin, nestin, vementin, smooth muscle alpha actin or a combination thereof.

In yet another embodiment of the present invention, an isolated hepatic stellate precursor cell which expresses both VCAM antigen and β3-integrin antigen is provided. In still further yet another embodiment of the present invention, a method of clonogenic expansion of stellate precursor cells is provided comprising culturing isolated stellate precursor cells expressing both VCAM antigen and β3-integrin antigen in serum-free media. The media may further comprise a growth factor, such as, for example, insulin, transferrin, leukemia inhibitory factor (LIF) or epidermal growth factor (EGF) or a combination thereof. The isolated stellate precursor cells may be further cultured in the presence of feeder cells, for example, STO cells.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE INVENTION

Figure 1:
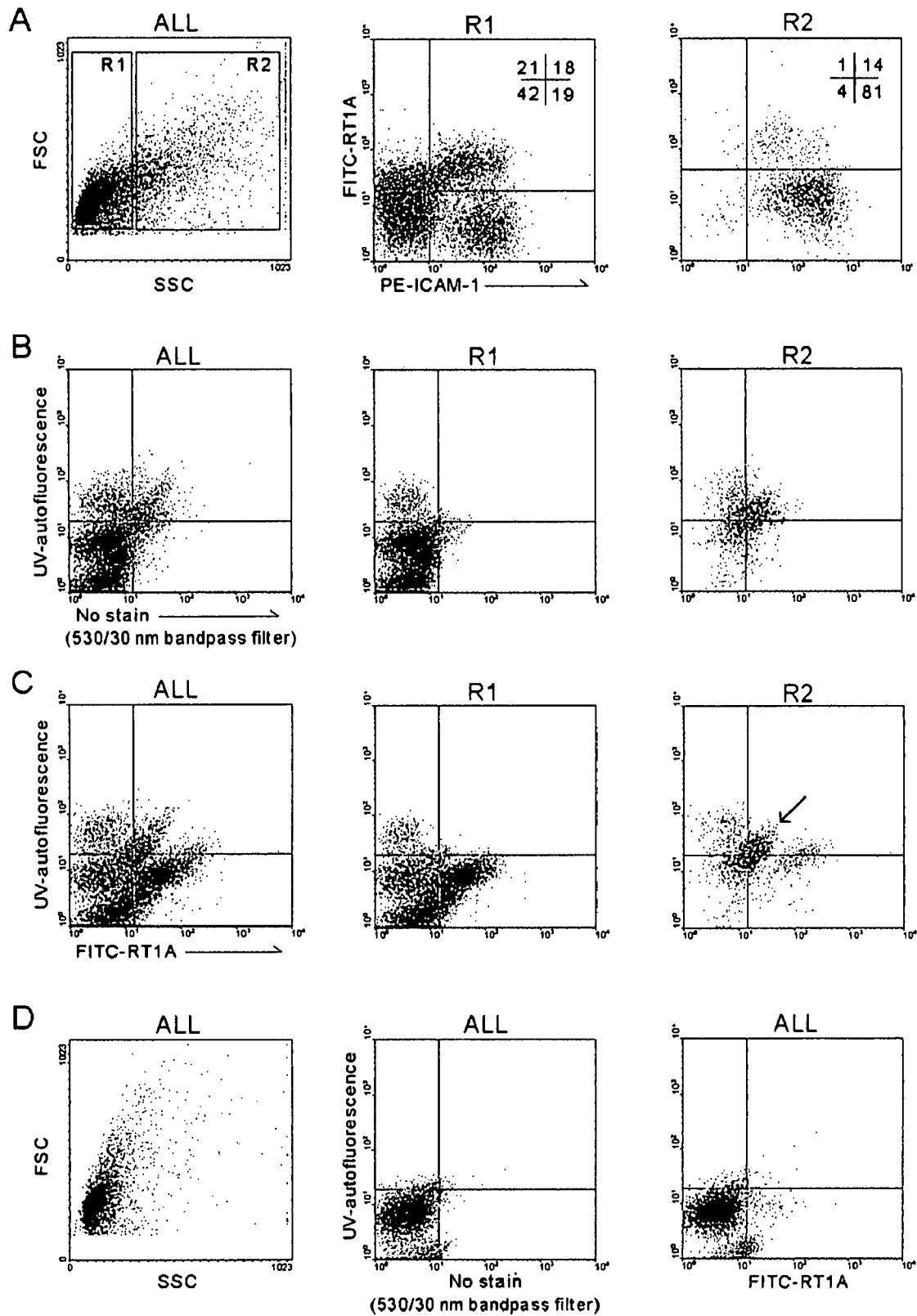
FIG. 1 shows flow cytometric analysis for autofluorescent cells in 13 dpc rat fetal liver and lung. (A) The pattern of forward scatter (FSC) and side scatter (SSC) of the entire population (ALL). Based on the value of SSC, R1 and R2 gates were created and represented high ($SSC^{hi}$) and low ($SSC^{lo}$) SSC, respectively. Expression patterns of RT1A and ICAM-1 in the R1 and R2 are also shown. $RT1A^-ICAM-1^+$ $SSC^{hi}$ cells (R2, lower right) are hepatoblasts in the rat fetal liver (Kubota and Reid, 2000). The number indicates percentage of each quadrant. (B) The autofluorescent pattern of entire population (ALL), R1, and R2 were analyzed with UV laser and 488 nm laser. UV laser specific autofluorescent signal was detected with a 450 nm filter, while non-specific autofluorescent signal excited with a 488 nm laser was measured with a 530/30 bandpass filter. UV laser-specific autofluorescent cells were detected in R1 and R2 (upper left). (C) Expression of RT1A and UV laser specific autofluorescent signal was studied. UV laser-specific autofluorescent cells were $RT1A^-$. ns-autoflu$^+$RT1A$^-$ cells (allow) were identified and were correspond to rat hepatoblast population. (D) UV laser specific autofluorescent signal was analyzed in 13 dpc fetal lung cells. There are no UV specific autofluorescent cells in the lung cell population. Most of all cells are $RT1A^-$, and no non-specific autofluorescent cells (comparable to the hepatoblast population in the fetal liver) were detected.

HpStCs have been assigned various names, including "lipocytes," "fat-storing cells," "Ito cells," "peri-sinusoidal cells," and "liver pericytes." In the interest of clarity, however, only the term HpStC will be used in this paper, which should nonetheless be understood to refer to the same population of cells having any and all of the aforementioned alternate names. As well, the teachings herein are not limited to any one species. In fact, it should be understood that the examples provided herein are merely exemplary and should not be construed as limiting. The instant invention, in this way, is not limited by its mammalian source for liver tissue. Mammals from which the HpStCs and their precursors may be derived include, but are not limited to, humans, rodents (e.g., rats, mice, hamsters), rabbits, bovines, horses, pigs, and sheep. Preferably, the HpStCs and their precursors are derived from humans. Nor is the instant invention limited to any particular stage of liver development. Thus, the instant invention may be practiced with fetal, neonatal, pediatric and/or adult liver tissue, including liver tissue from recently deceased individuals (e.g., less than about 30 hours post mortem).

The instant invention provides techniques for the isolation and propagation of HpStC precursor cells (also referred to herein as "HpStC precursors" or "precursor HpStCs"). HpStC precursors in rat fetal liver were identified by flow cytometry using the specific auto-fluorescence generated by cytoplasmic vA rich lipid droplets. The surface phenotype of $vA^+$ cells appeared to be uniform, and they were $RT1A^-$ $ICAM-1^+VCAM-1^+\beta3\text{-integrin}^+PECAM-1^-$. In addition to those surface markers, $vA^+$ cells express intermediate filaments specific for HpStCs including desmin, vimentin, SMαA, and nestin.

Although ICAM-1 expression on fetal liver cells is broad, β3-integrin is relatively specific on $vA^+$ cells. β3-integrin requires α-integrin, αv-integrin or αII-integrin, for the surface expression. The choice varies with the cell types. In the case of HpStCs in adult liver, αv-integrin is used for the α-chain. Therefore, it is likely that HpStC precursors express αv-integrin. Interestingly, interaction of αvβ3-integrin expressed on adult HpStCs and the ECM ligands appeared to influence the fate determination of HpStCs, proliferation or apoptosis. The αvβ3-integrin transduced a stimulatory signal to protect apoptotic responses in adult HpStCs. In addition, another report showed that αvβ3-integrin binds PECAM-1. Thus, without being limited to or bound by theory, β3-integrin expression on HpStC precursors seems to be important to receive stimulatory signals from surrounding ECM ligands or endothelial cells, which express PECAM-1, for proliferation during fetal liver development.

While FACS analysis indicated that high VCAM-1 expression was detected on hepatoblasts and HpStC precursors in fetal liver, the later may play more important roles for hematopoietic cells, because they express SDF-1α as well. SDF-1α is a potent chemoattractant for hematopoietic stem cells, which express CXCR4, the receptor for SDF-1α. The chemokine plays a central role during the migration of hematopoietic stem/progenitor cells to bone marrow and is thought to up-regulate VLA-4 dependent adhesion to VCAM-1. Therefore, it is possible that SDF-1α and VCAM-1 expression on HpStC precursors are crucial to recruit hematopoietic stem/progenitor cells into fetal liver.

Interestingly, VCAM-1 is expressed on hepatoblasts. In addition to the surface phenotype and mRNA expression, in vitro CFA for hepatoblasts demonstrated that $VCAM-1^+$ cells are hepatoblasts. This finding is unexpected because VCAM-1 is known as a surface marker for mesenchymal cells such as endothelial cells, myogenic cells, or HpStCs. The expression appears to be developmentally controlled because adult hepatocytes are $VCAM-1^-$ by FACS analysis.

It appears that HpStC precursors are important for liver development, because they are major HGF producers in the fetal liver. HGF is a crucial growth factor for hepatic development, and the factor is responsible for liver parenchymal cell growth during liver regeneration as well. In addition, it has been shown that HpStCs, but not parenchymal cells, endothelial cells, and Kupffer cells, express HGF in adult liver. Therefore, our data and previous studies suggest that HpStCs are main HGF producers from fetuses to adults in the liver. Thus, HpStC precursors likely play a crucial role for hepatic and hematopoietic development in the fetal liver because the cells are main producers for HGF and SDF-1α.

Considering the unique phenotypic and functional characteristics of HpStC precursors including expression of VCAM-1 and H1x and production of HGF and SDF-1α, the precursors might consist of a stem cell niche for hematopoietic stem cells or hepatic stem cells, or both in the liver. Because the serum-free culture system maintained the unique characteristic phenotypes of HpStC precursors in vitro, the culture system can be use to develop an in vitro colony assay system to identify HpStC precursors from adult livers. In addition, if a HpStC transplantation system is developed, cell therapy using HpStC precursors will be feasible. Identification, ex vivo expansion, and transplantation of HpStC precursors or HpStC progenitors in adult liver, would be a valuable resource to replace activated HpStCs in fibrogenic liver. Clearly, phenotypic identification and an in vitro culture system for HpStC precursors described in this study demonstrate a new direction to develop novel therapeutic approaches for liver diseases.

The following examples are illustrative of the invention, but the invention is by no means limited to these specific examples. A person of ordinary skill in the art will find in these examples but one means to implement the instant invention. Further, while the instant examples have been presented in the context of rats for experimental convenience, the methods and reagents described herein can be readily translated to human application(s) by one of ordinary skill in the art from the teachings disclosed below.

Materials and Methods

Rats

Pregnant Fisher 344 rats were obtained from the Charles River Breeding Laboratory (Wilmington, Mass.). The morning on which the plug was observed was designated day 0. Male Fisher 344 rats (200-250 g) were used for isolation of adult HpStCs. All animal experiments were conducted under the institutional guidelines, and The University of North Carolina Institutional Animal Care and Use Committee approved all experimental procedures in accordance with *The Guide for Care and Use of Laboratory Animals* of the National Academy of Sciences.

Cell Preparation

Hepatic progenitors suitable for in vitro propagation in accordance with the instant invention are not limited to those isolated or identified by any particular method. In general, HpStC precursors may be obtained from any excised section of liver. The excised section of liver may then be dissociated by standard procedures into single dissociated cells. Such procedures include enzymatic dissociation and/or mechanical dissociation. Enzymatic dissociation may be carried out in the presence of protease(s), such as collagenase(s), and/or nuclease(s), such as DNase. In some instances, pronase(s) may also be used. Methods of enzymatic dissociation of liver cells are described and practiced in the art. By way of example, methods for the isolation and identification of the hepatic progenitors have been described in, for example, U.S. Pat. No. 6,069,005 and U.S. patent application Ser. Nos. 09/487,318; 10/135,700; and 10/387,547, the disclosures of which are incorporated herein in their entirety by reference. Indeed, various procedures exist for digestion and isolation of single cell suspensions of liver cells. It is to be understood, therefore, that the scope of the present invention is not to be limited to a specific method of procuring whole livers or preparing single cell suspensions thereof.

In the instant Examples, fetal livers were isolated from 13~14 dpc rats and digested with 800 U/ml collagenase (Sigma) followed by further digestion with Trypsin-EDTA solution (Sigma). The cell suspension was treated with 200 U/ml DNase I (Sigma) (Kubota and Reid, 2000).

Cell Culture

In a preferred embodiment, the in vitro propagation steps involve using a serum-free, hormone-supplemented, defined medium (HDM) to support the propagation of HpStC precursor cells on a layer of feeder cells. The function of the feeder cells is multi-fold, including supplying nutrients, supplying an attachment surface, and secreting into the medium certain growth factors and extracellular matrix components needed for survival, growth and/or differentiation of the precursor HpStCs. The feeder cells may be from reptiles, birds, crustaceans, fish, annelids, molluscs, nematodes, insects, or mammals, preferably human. More preferably, the feeder cells derive from embryonic tissue, and more preferably, embryonic liver tissue. Fetal liver cells were cultured on STO cell feeders and in a serum-free hormonally defined medium as described previously (Kubota and Reid, 2000).

HDM consists of a 1:1 mixture of Dulbecco's modified Eagle's medium and Ham's F12 (DMEM/F12, GIBCO/BRL) to which was added 2 mg/ml bovine serum albumin (Sigma), 5 µg/ml insulin (Sigma), $10^{-6}$ M dexamethasone (Sigma), 10 µg/ml iron-saturated transferrin (Sigma), $4.4 \times 10^{-3}$ M nicotinamide (Sigma), $5 \times 10^{-5}$ M 2-mercaptoethanol (Sigma), 7.6 µeq/l free fatty acid, $2 \times 10^{-3}$ M glutamine (GIBCO/BRL), $1 \times 10^{-6}$ M $CuSO_4$, $3 \times 10^{-8}$ M $Na_2SeO_3$ and antibiotics (penicillin and streptomycin). Free fatty acids comprised palmitic, palmitoleic, stearic, oleic, linoleic, and linolenic acids (all Sigma) in the respective millimolar proportions of 31.0:2.8:11.6:13.4:35.6:5.6 for 100 meq/l stock solution.

STO feeder cells were prepared as previously described (Kubota and Reid, 2000). Briefly, a subclone of STO cells, STO5, was transfected with pEF-H1x-MC1neo. A transfected clone, STO5H1x, were treated with mitomycin C (Sigma) and used for feeder cells at concentration of $2 \times 10^5$ cell per well in a 12-well plate. For long-term culture of sorted vA$^+$ cells, cells were cultured on STO feeders and in HDM supplemented with 10 ng/ml human leukemia inhibitory factor (LIF; Boehringer Mannheim) and 10 ng/ml epidermal growth factor (EGF; Collaborative Biomedical Product). Medium was changed every other day, and cells were subcultured to fresh STO feeders every week.

Immnocytochemical Staining of Colonies

Staining procedures for cultured cells were described previously (Kubota and Reid, 2000). Briefly, culture plates were fixed in methanol-acetone (1:1) for 2 min at room temperature, rinsed and blocked with 20% goat serum (GIBCO/BRL) at 4° C. For double labeling of albumin (ALB) and cytokeratin (CK) 19, cultures were incubated with anti-rat ALB antibody (ICN Biomedicals) and anti-cytokeratin 19 (CK19) monoclonal antibody (Amersham) followed by Texas Red-conjugated anti-rabbit IgG (Vector laboratories) and FITC-conjugated anti-mouse IgG (Caltag). For nestin or desmin expression, cells were stained with anti-nestin antibody (Rat-401, Developmental Studies Hybridoma Bank, The University of Iowa) or anti-desmin antibody (D33, Dako) followed by Alexa488-conjugated anti-mouse IgG (Molecular Probes).

Fluorescence-Activated Cell Sorting (FACS)

Cells were analyzed and sorted by a FACStar Plus cell sorter (BD Biosciences) equipped with dual Coherent I-90 lasers. To detect vA-specific autofluorescence, cells were excited at 351 nm, and fluorescence emission was detected with the use of 450DF20 filter (Omega Optical Inc, Brattleboro, Vt.). Fluorescence-conjugated antibodies were excited at 488 nm, and their fluorescence emission was detected by standard filters.

Monoclonal antibodies used for analysis of rat cells were FITC-conjugated anti-RT1A (B5; BD Biosciences), phycoerythrin (PE)-conjugated anti-rat ICAM-1 (1A29; BD Biosciences), anti-rat VCAM-1 (5F10, Babco), anti-rat α6β1-integrin (mAB-5A, Serotec), anti-rat CD44 (OX-49, BD Biosciences), PE-conjugated anti-rat VCAM-1 (MR109; BD Biosciences), PE-conjugated or biotin-conjugated anti-rat β3-integrin (2C9.G2; BD Biosciences), biotin-conjugated anti-rat PECAM-1 (TLD-3A12; BD Biosciences), biotin-conjugated anti-rat Thy-1 (OX-7; BD Biosciences). To block non-specific antibody binding, cells were incubated with 20% goat serum (GIBCO/BRL), 1% teleostean gelatin (Sigma), and anti rat CD32 (FcγII receptor) antibody (D34-485, Rat BD Fc Block™, BD Biosciences) solution prior antibody staining in FACS experiments. For staining with unconjugated anti-VCAM-1 antibody (5F10), fetal liver cells were incubated with the anti-VCAM-1 antibody followed by staining with biotin-conjugated anti-mouse $IgG_{2a}$ monoclonal antibody (R19-15, BD Biosciences). Streptavidin-Cy-Chrome (BD Biosciences) was used to detect biotin-conjugated antibodies.

For the experiments of FACS to isolate long-term cultured cells that were derived from sorted vA$^+$ cells, all cells in the culture were harvested and stained with biotin conjugated anti-mouse CD98 (H202-141, BD Biosciences) followed by streptavidin-Cy-Chrome to separate cultured rat cells and STO feeder cells. Murine STO feeder cells were stained brightly with the antibody against mouse CD98. Thus, CD98-negative cells represent rat-derived cells and could be distinguished readily using FACS as shown previously (Kubota and Reid, 2000).

Colony Forming Assay (CFA) for Hepatoblasts

The procedure of CFA for hepatoblasts was described previously (Kubota and Reid, 2000). Briefly, sorted cells were plated on STO feeders in triplicate at 500 or 2500 cells/well (3.8 cm$^2$) in a 12-well plate and cultured in HDM for 14~15 days with medium changes every other day. To examine bipotential differentiation activity of hepatoblasts, double immunofluorescence staining of ALB and CK19 was performed. The colonies were stained by Diff-Quick (Baxter) to count the number of the colonies per well.

Cell Proliferation Assay vA$^+$ cells isolated by FACS were plated in triplicate at 500 cells/well in a 96-well plates with HDM supplemented with laminin (Collaborative Biomedical Products) at the final concentration of 8 µg/ml. EGF and LIF were added at concentrations indicated. Five days after plating cells cultures were rinsed twice to remove floating cells and added fresh medium with the tetrazolium salt WST-1 (Boehringer Mannheim) to measure the number of viable adherent cells (Kubota and Reid, 2000). After 4 hours, the absorbance was determined according to the manufacturer's protocol.

Reverse Transcriptase-Polymerase Chain Reaction (RT-PCR)

The primer sequences used for PCR are shown in Table 1.

TABLE 1

| Target | Sequence | | Number of amplification |
|---|---|---|---|
| desmin | Sense | 5'-ATGAGCCAGGCCTACTCGTCC-3' | 35 |
| | Anti-sense | 5'-CAGCACTTCATGTTGTTGCTG-3' | |
| nestin | Sense | 5'-TGGAACAGAGATTGGAAGGCC-3' | 35 |
| | Anti-sense | 5'-CAGGAGTCTCAAGGGTATTAG-3' | |
| vimentin | Sense | 5'-TCCAACCGGAGCTATGTGACC-3' | 30 |
| | Anti-sense | 5'-CTCAGGTTCAGGGAAGAAAAG-3' | |
| SMαA | Sense | 5'-ATGTGTGAAGAGGAAGACAGC-3' | 30 |
| | Anti-sense | 5'-GTGGTTTCGTGGATGCCCGC-3' | |
| albumin | Sense | 5'-ATGAAGTGGGTAACCTTTCTCC-3' | 26 |
| | Anti-sense | 5'-TGTGATGTGTTTAGGCTAAGGC-3' | |
| Prox-1 | Sense | 5'-GGGGAAAACCACAATTTCCACAC-3' | 33 |
| | Anti-sense | 5'-CCAGGAAGGATCAACATCTTTGC-3' | |
| SDF-1α | Sense | 5'-ATGGACGCCAAGGTCGTCGC-3' | 30 |
| | Anti-sense | 5'-GAAAGGGTCTCTGAGCACAG-3' | |
| HGF | Sense | 5'-TGGACAAGATTGTTATCGTGG-3' | 33 |
| | Anti-sense | 5'-ACGATTTGGGATGGCACATCC-3' | |
| Hlx | Sense | 5'-CCTCGGTCCAGTCTATAAACC-3' | 30 |
| | Anti-sense | 5'-CAGCCGTTCTGAGGGCGAAGC-3' | |
| β3-integrin | Sense | 5'-GATGAAAAAATTGGCTGGAGG-3' | 33 |
| | Anti-sense | 5'-GCAGGTGGCATTGAAGGACAG-3' | |
| GFAP | Sense | 5'-CTCAATGACCGCTTTGCTAGC-3' | 35 |
| | Anti-sense | 5'-ACCACGATGTTCCTCTTGAGG-3' | |
| β-actin | Sense | 5'-ATGGATGACGATATCGCTGCG-3' | 26 |
| | Anti-sense | 5'-GGGTGTAAAACGCAGCTCAGTAA-3' | |

The procedure of RT-PCR for sorted cells by FACS was described previously (Kubota et al., 2002). Briefly, cells were isolated using a FACStar Plus cell sorter, and total RNAs were extracted by RNeasy Kit (QIAGEN) and subjected to cDNA synthesis. cDNAs were synthesized from total RNAs by oligo-dT priming and AMV reverse transcriptase (Seikagaku America) in a reaction volume of 20 μl at 42° C. (Kubota et al., 2002). PCR was performed in a total volume of 50 μl consisting of 1 μM each primer, 200 μM each dNTP, 50 mM KCl, 1.5 mM $MgCl_2$, 10 mM Tris HCl, pH 8.3, and 1.25 U Amplitaq polymerase gold (Perkins Elmer) with synthesized cDNA. Samples were heated to 94° C. for 3 min followed by amplification for 26-35 cycles of 2 min at 94° C., 2 min 62° C., and 3 min at 72° C. The number of amplification cycles for each target gene was varied and indicated in Table 1. After the last cycle, a final extension step was done at 72° C. for 6 min. Then, 5 μl of each PCR reaction was analyzed by 1% agarose gel electrophoresis. cDNAs synthesized from total RNAs of sorted cells were normalized by the cell number.

Results

Identification of Vitamin A+ Cells in Fetal Liver

Once a single cell suspension has been established, isolation of HpStC precursors involves exposing the mixed liver cell populations derived from liver tissue to flow cytometry and selecting those cells that exhibit specific auto-fluorescence generated by cytoplasmic vitamin A (vA) rich lipid droplets. Vitamin A specifically produces a green-blue fluorescence when excited with light of 330-360 nm (ultra violet, UV) laser. FACS analysis is able to detect the vitamin A-specific green-blue fluorescence ($vA^+$) in the cytoplasm of both mature HpStCs as well as precursor HpStCs in liver using a UV laser.

FIG. 1A shows the pattern of autofluorescence in the 13 dpc fetal liver cells. The vA-specific, blue-green autofluorescent signal was measured by detecting the emission light with a 450 nm filter by excitation of a UV laser (351 nm). To detect a non-UV laser-specific autofluorescent signal, a 488 nm laser and 530/30 nm bandpass filter was used. Patterns of the autofluorescent signals of whole fetal liver cell population as well as two subpopulations (R1 and R2 gates of FIG. 1A) are shown in FIG. 1B. In the FACS pattern of the whole cell population (FIG. 1B ALL), two distinct subpopulations with high autofluorescent characteristics were identified. One had an autofluorescent signal specific for UV light (FIG. 1B ALL, upper left), which is referred to as $vA^+$ here, whereas cells locating diagonally in the upper right quadrant indicate non-specific autofluorescence, because the autofluorescent signals were detected with the 530 nm filter and the 450 nm filter when excited by the 488 nm laser and the UV laser, respectively. The subpopulation with non-specific autofluorescent characteristics (designated as ns-autoflu+) exclusively derived from the $SSC^{high}$ gate (FIG. 1A, R2 and FIG. 1B, R2) while vA+ cells (FIG. 1B, upper left) were detected in both R1 and R2.

FIG. 1C shows the pattern of vA-specific autofluorescent signal and MHC class Ia expression, which was detected by a FITC-conjugated antibody against RT1A. FACS analysis indicated that vA+ cells as well as ns-autoflu+ cells had no RT1A expression, because those two populations did not shift in the stained sample (FIG. 1C, R2) compared to the control sample (FIG. 1B, R2). In addition, FACS analysis also indicated that the hepatoblast population, cells that are RT1A−ICAM-1+SSC$^{high}$ (FIG. 1A R2, lower right) and RT1A−ns-autoflu+ cells (FIG. 1C R2, arrow) are an overlapping population by this FACS analysis.

To determine whether these autofluorescent signals were specific in fetal liver, fetal lung cells from the 13 dpc fetuses were isolated and analyzed by FACS. The FACS analysis showed there were neither ns-autoflu+ cells nor vA+ cells in the lung cells (FIG. 1D), indicating that the autofluorescent signals in particular subpopulations in the fetal liver were unique phenotypic characteristics.

As hepatic progenitor cells (i.e., hepatoblasts) have been suggested to be RT1A−OX18$^{low}$ICAM-1+SSC$^{high}$ cells in 13 dpc liver of rat fetus, these markers were assayed in vA+ cells. FIG. 1A shows the patterns of FACS analysis of fetal liver cells at 13 dpc followed staining with antibodies against RT1A, rat MHC class I, and ICAM-1. FIG. 1C shows the pattern of vA− specific autofluorescent signal and RT1A expression, which was detected by FITC-conjugated antibody against RT1A. FACS analysis indicated that vA+ cells as well as ns-autoflu+ cells had no RT1A expression, because those two populations did not shift in the stained sample (FIG. 1C, R2) compared to the control sample (FIG. 1B, R2). In addition, FACS analysis indicated that the hepatoblast population, cells that are RT1A−ICAM-1+SSC$^{high}$, (FIG. 1A, R2, lower right) and RT1A−ns-autoflu+ cells (FIG. 1C, R2, arrow) were an identical population. These results indicate that FACS analysis was able to detect characteristic vA+ cells in rat fetal liver as early as 13 dpc and that the vA+ cells were RT1A-ICAM-1+.

Vitamin A+ Cells Express VCAM-1 and Integrin β3

As demonstrated above, vA positivity and MHC class Ia negativity are sufficient markers to identify and isolate HpStCs. However, in some circumstances UV selection based on UV light may not be desirable, particularly where molecular (e.g., DNA) integrity is of concern. Therefore, the present invention provides markers that may be used in addition to or in lieu of UV-based selection. HpStC precursors can be further identified by exposing the selected cell population to antibodies specific for VCAM, more specifically VCAM-1. VCAM-1 is significant because it has been shown to be a unique surface marker distinguishing HpStCs from myofibroblasts in adult liver. As well, the expression of VCAM-1 appears to be developmentally controlled because adult hepatocytes are negative for this marker.

Figure 2:
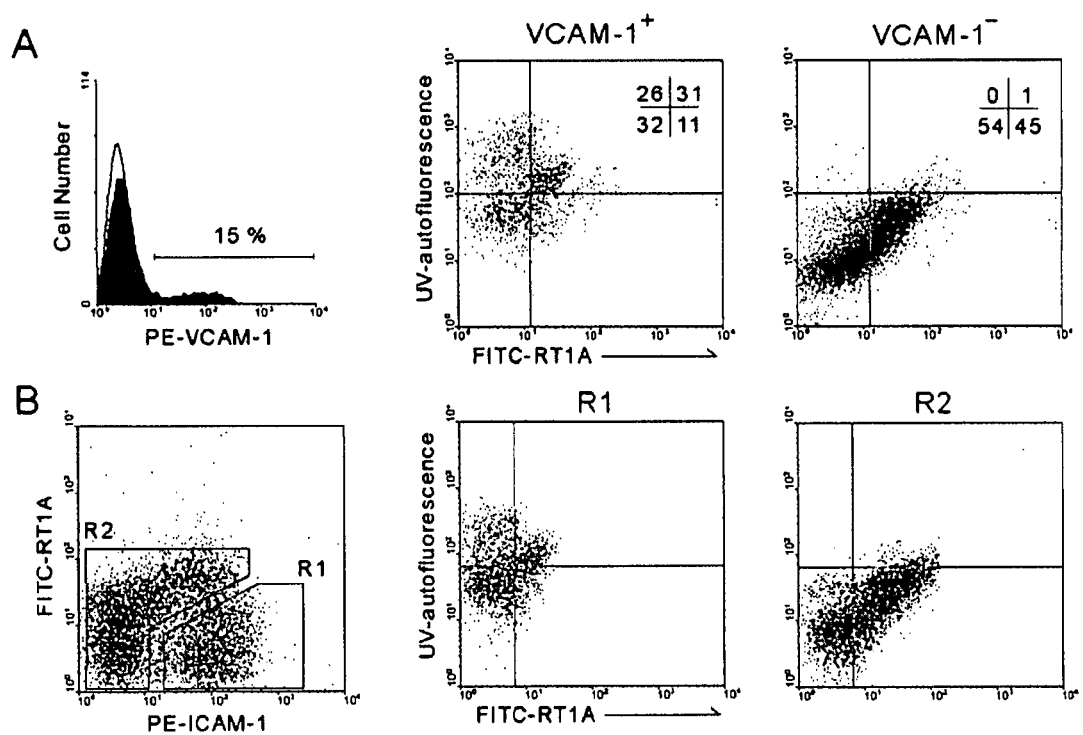
FIG. 2 shows VCAM-1 and ICAM-1 expression on $vA^+$ cells. (A) Histogram of flow cytometry for VCAM-1 expression on 13 dpc fetal liver. Approximately 15% of cells express VCAM-1 on the cell surface. Closed and open histograms represent stained cells and unstained cells, respectively. $VCAM-1^+$ and $VCAM-1^-$ cells were analyzed by flow cytometry for their autofluoresent signals. All $vA^+$ cells and ns-autoflu$^+$ cells are VCAM-1 positive. The numbers represent the percentage of each quadrant. (B) Two color analysis of 13 dpc fetal liver cells for RT1A and ICAM-1. R1 cell population ($RT1A^-ICAM-1^+$) contains all $vA^+$ cells and ns-autoflu$^+$ cells. These results indicate that $vA^+$ and ns-autoflu$^+$ cells are $VCAM-1^+RT1A^-ICAM-1^+$.

VCAM-1 expression was analyzed in fetal liver cells to investigate whether the vA+ cells express VCAM-1. By FACS analysis, it appeared that about 15% of cells were VCAM-1+ in the 13 dpc fetal liver (FIG. 2A). The pattern of autofluorescence and RT1A expression of the VCAM-1+ cells was next determined. VCAM-1+ cells contained essentially all vA+ cells as well as the entire ns-autoflu+ cell population (FIG. 2A), indicating that HpStCs and hepatoblasts express VCAM-1. FACS analyses of two monoclonal antibodies against rat VCAM-1 (5SF10 and MR109) showed an identical pattern of VCAM-1 expression. In addition, fetal liver VCAM-1+ cells were RT1A−ICAM-1+ cells because the R1 gate in FIG. 2B included the VCAM-1+ cell population. These results suggest that fetal liver VCAM-1+RT1A−ICAM-1+ cells consist of vA+ cells, hepatoblasts, and some non-autofluorescent cells.

Additional surface antigens were investigated to distinguish the two autofluorescent populations, the vA+ cells and the hepatoblasts, both of which were VCAM-1+RT1A−ICAM-1+ cells. Because β3-integrin (CD61) is expressed on endothelial cells, vascular smooth muscle cells, and adult HpStCs, two-color FACS analyses of VCAM-1 versus integrin β3 were performed. The majority of vA+RT1A− cells expressed β3-integrin whereas ns-autoflu+RT1A− cells were β3-integrin−, while vA−RT1A− cells contained some VCAM-1+β3-integrin+ cells (FIG. 3B).

Autoflu−RT1A− cells contained some VCAM-1+β3-integrin+ cells. The remaining major population (FIG. 3B, R4) was VCAM-1− and appeared to be correspond to R2 cell population in FIG. 2B. The R4 cell population comprised non-adherent cells when they were cultured on plastic dishes, suggesting that they were hematopoietic cells. A subpopulation (~20%) of the fraction was β3-integrin+. Expression of PECAM-1 (CD31), which is known as an endothelial cell marker, was also assessed. However, FACS analysis indicated that PECAM-1 expression in vA+RT1A− cells and ns-autoflu+RT1A− cells was negligible (FIG. 3B), while PECAM-1+ cells were detected in the autoflu−RT1A− and non-adherent cell populations (FIG. 3B, R2 and R4). Expression of Thy-1 (CD90), a surface marker for oval cells that appear in adult livers after oncogenic insults, was further assessed. FACS analysis showed that ns-autoflu+ RT1A− are Thy-1−.

By contrast, vA+ RT1A− cells, autoflu−RT1A− cells and non-adherent cells express Thy-1 heterogeneously. FACS analysis indicated that ns-autoflu+ RT1A− cells were CD44$^{lo}$ whereas vA+ RT1A− cells were CD44− (data not shown). Although CD44 (Pgp-1) appeared to be expressed differentially in the vA+RT1A− cells and ns-autoflu+RT1A−, the expression on the cell surface was weak. Together, these data suggest that β3-integrin antibody staining, among all antibodies examined, facilitate distinguishing the vA+RT1A− cells and ns-autoflu+RT1A− cells, both of which populations were VCAM-1+ICAM-1+ in the fetal livers.

VCAM-1+ Integrin β3− Non-Specific Autofluorescent Cell Population Contains Only Hepatoblasts Fetal hepatic cells of the rat until 14 dpc are homogeneous with developmental potential to differentiate to both the hepatocytes and biliary epithelial cells depending upon the microenvironment. These bipotent progenitors are called hepatoblasts. To examine whether vA+ cells have any potential to generate hepatic cell lineages, the CFA (Kubota and Reid, 2000) was performed. Four cell populations were isolated by FACS and subjected to the CFA for hepatoblasts: 1) ns-autoflu+RT1A−VCAM-1+β3-integrin−2) vA+RT1A−VCAM-1+3) autoflu−RT1A− and 4) VCAM-1− non-adherent cells. Sorted cell fractions were placed on STO5 feeders in HDM, cultured for 15 days, and stained with antibodies against albumin and CK19 for hepatic and biliary lineages, respectively. Then, all hepatic colonies were counted.

Figure 4:
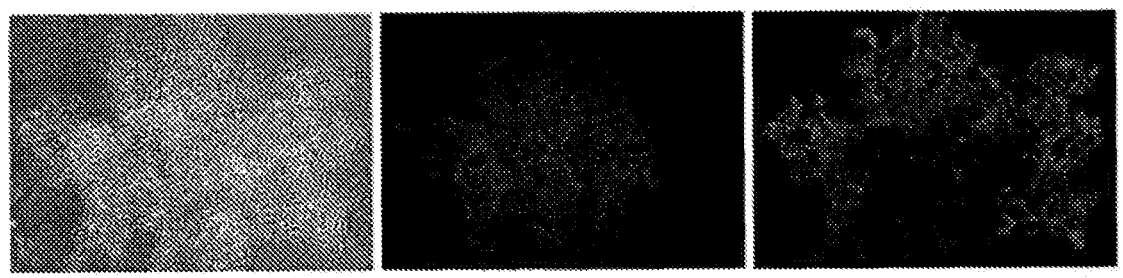
FIG. 4 shows immunocytochemistry of a bipotent hepatblast colony. ns-autoflu$^+$VCAM-1$^+$ cells were isolated by FACS and placed on STO feeder cells in HDM at a clonal cell density (250 cells in a well of 12-well plate; 66 cells/cm$^2$). After 15 days in culture, the cells were fixed and stained with antibodies against ALB (red) and CK19 (green). Each colony was generated from a single sorted cell (Kubota and Reid, 2000). More than 95% (95.7±0.4%; mean±SEM, n=3) of hepatic colonies contained $ALB^+CK19^-$ and $ALB^-CK19^+$ cells, which represent hepatocytic and biliary differentiation, respectively.

The CFA indicated that hepatic colonies were generated from group 1, ns-autoflu+VCAM-1+β3-integrin− cells (Table 2, below), demonstrating that the other groups of sorted cells, including the vA+VCAM-1+β3-integrin+ cells, are not hepatic progenitors. More than 95% of the hepatic colonies derived from the group 1-sorted cells contained both hepatocytic (albumin+CK19−) and biliary epithelial (albumin−CK19+) cells (FIG. 4). Further, the colony forming efficiency in the sorted ns-autoflu+VCAM-1+β3-integrin− cells was approximately 31%, and a hepatic progenitor cell line (rhe14321) established in a previous study (Kubota and Reid, 2000) had a colony efficiency in the CFA of 42.5±1.8%. Taken together, the result of CFA in this experiment indicated that the the ns-autoflu$^+$VCAM-1$^+$β3-integrin$^-$ cells population is a nearly pure hepatoblast population, because CFAs by established cell lines is presumably much higher than that of freshly isolated cells.

Figure 3:
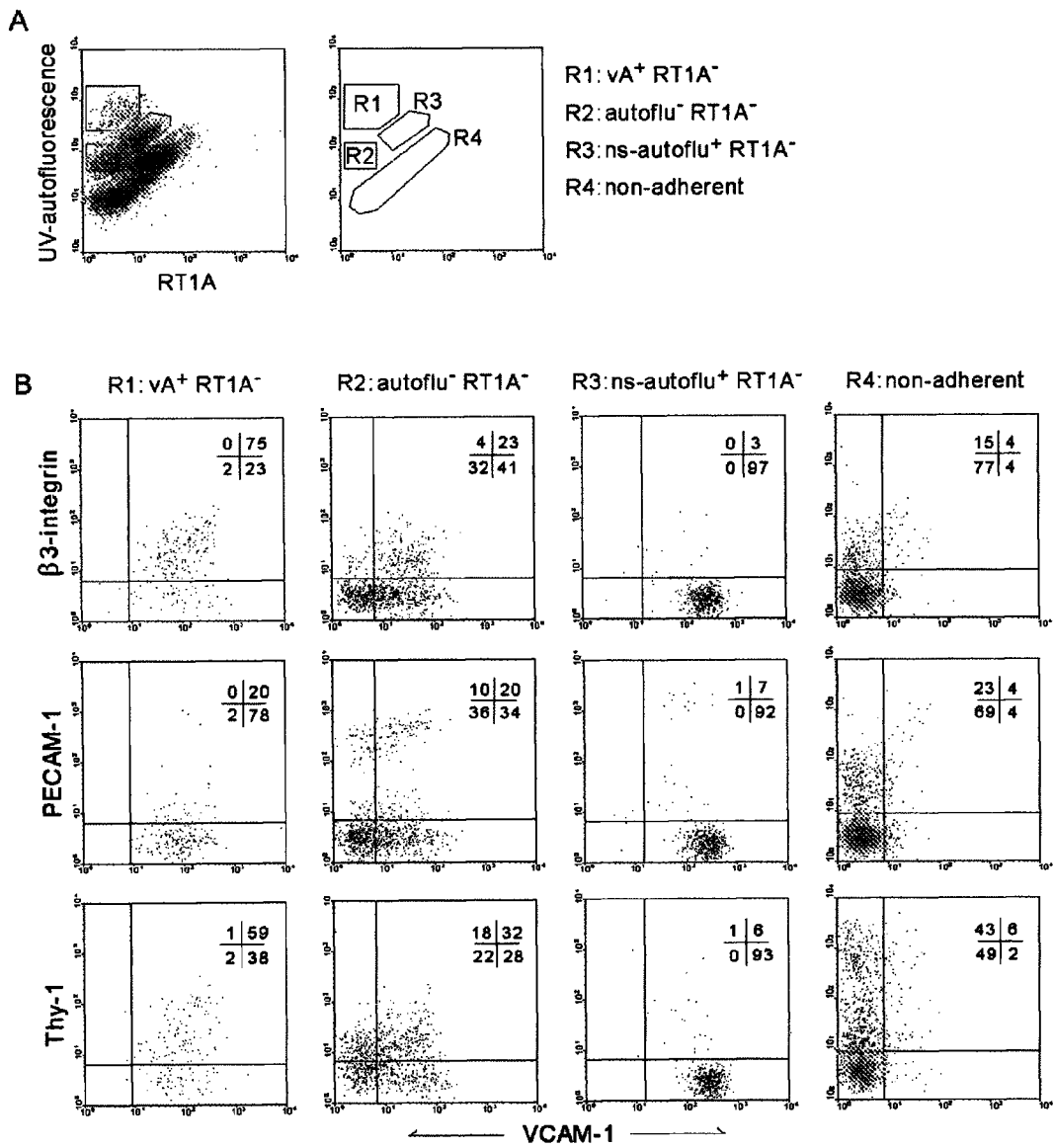
FIG. 3 shows antigenic profiles of $vA^+$, ns-autoflu$^+$, and autoflu$^-RT1A^-$ cells in 13 dpc fetal liver. (A) Flow cytometric analysis for UV-autofluorescence and RT1A expression. In the $RT1A^-$ cell population, four gates (R1-R4) were created based on the autofluorescent signals. (B) Two color analysis of VCAM-1 versus β3-integrin, PECAM-1, or Thy-1 expression for each gated cell population (R1-R4). The numbers represent the percentage of each quadrant. Primarily R1 cells are $VCAM-1^+β3-integrin^+$, while R3 cells uniformly express VCAM-1, but none of β3-integrin, PECAM-1, or Thy-1.

Table 2 provides the frequency of hepatic stellate colonies from sorted rodent fetal liver cells. Gates for fractionation of vA$^+$RT1A$^-$VCAM-1$^{30}$, autoflu$^-$RT1A$^-$, ns-autoflu$^+$RT1A$^-$ and VCAM-1$^-$ cells were created as shown in FIG. 3 R1, R2, R3 and R4, respectively.

| Cell Population | Inoculated cell number | Hepatic colony number | Colony efficiency (%) |
|---|---|---|---|
| vA$^+$ RT1A$^-$ VCAM-1$^+$ β3-integrin$^+$ ¶ | 2500 (6) | 3.3 ± 0.9 | 0.1 ± 0.0 |
| autoflu$^-$ RT1A$^-$ | 2500 (6) | 5.5 ± 0.2 | 0.2 ± 0.1 |
| ns-autoflu$^+$ RT1A$^-$ VCAM-1$^+$ β3-integrin$^-$ § | 250 (6) | 77.0 ± 6.7 | 30.8 ± 2.7 |
| VCAM-1$^-$ † | 2500 (3) | 0.0 ± 0.0 | 0.0 ± 0.0 |

¶: VCAM-1$^+$ β3-integrin$^+$ cells from the R2 were sorted.
§: VCAM-1$^+$ β3-integrin$^-$ cells from the R1 were sorted.
†: VCAM-1$^-$ cells from the R4 were sorted.

Flow cytometrically sorted cells were cultured on STO feeders at indicated cell numbers per well in a 12-well plate. The hepatic colony number is the average per well. Colony efficiency is expressed as the percentage of cells inoculated in culture and that went on to form colonies after 15 days of culture. Values are mean±SEM. Number of total well inoculated sorted cells is enclosed in parentheses.

Gene Expression of Freshly Isolated Vitamin A$^+$VCAM-1$^+$ integrin β3$^+$ Cells Gene expression pattern of the vA$^+$RT1A$^-$VCAM-1$^+$β3-integrin$^+$ cells was next assayed to examine whether they express various markers for HpStCs. Five population were isolated by FACS, and RNAs were isolated from the five populations. RT-PCR for HpStC markers was perform using cDNAs synthesized from the RNAs. The five populations were: 1) ns-autoflu$^+$RT1A$^-$VCAM-1$^+$β3-integrin$^-$, 2) vA$^+$RT1A$^-$VCAM-1$^+$β3-integrin$^+$, 3) autoflu$^-$RT1A$^-$VCAM-1$^+$, 4) autoflu$^-$RT1A$^-$VCAM-1$^-$, and 5) VCAM-1$^-$ non-adherent cell population. HpStCs in adult liver express intermediate filaments, desmin and nestin, which are not expressed in other cell types in the liver.

RT-PCR analyses showed that vA$^+$RT1A$^-$VCAM-1$^+$β3-integrin$^+$, ns-autoflu$^+$RT1A$^-$VCAM-1$^+$, and autoflu$^-$VCAM-1$^-$ cells expressed all four intermediate filaments. ns-autoflu$^+$RT1A$^-$VCAM-1$^+$ cells express albumin as well as Prox1, which is a transcriptional factor expressing specifically in hepatoblasts. This result was consistent with the data obtained from the CFA assays, which demonstrated this population comprised hepatoblasts. There was no expression of nestin, SMαA, or vimentin in the hepatoblast population. The expression of HpStC specific intermediate filaments strongly suggests that vA$^+$ cells are HpStC precursors.

Subsequently, expression of three separate mesenchymal cell markers, HGF, stromal cell-derived factor-1 alpha (SDF-1α), and divergent homeobox transcriptional factor, H1x, were investigated using RT-PCR. HGF is required for normal hepatic development, especially for proliferation and differentiation of hepatoblasts in the mouse, and in adult liver HpStCs are major producers of HGF. SDF-1α is a potent chemokine for hematopoietic progenitors, and hematopoietic stem cells in fetal liver migrate in response to the chemokine. H1x is expressed in mesenchymal cells in developing fetal liver and plays an indispensable role in fetal liver hematopoiesis and hepatic development.

Figure 5:
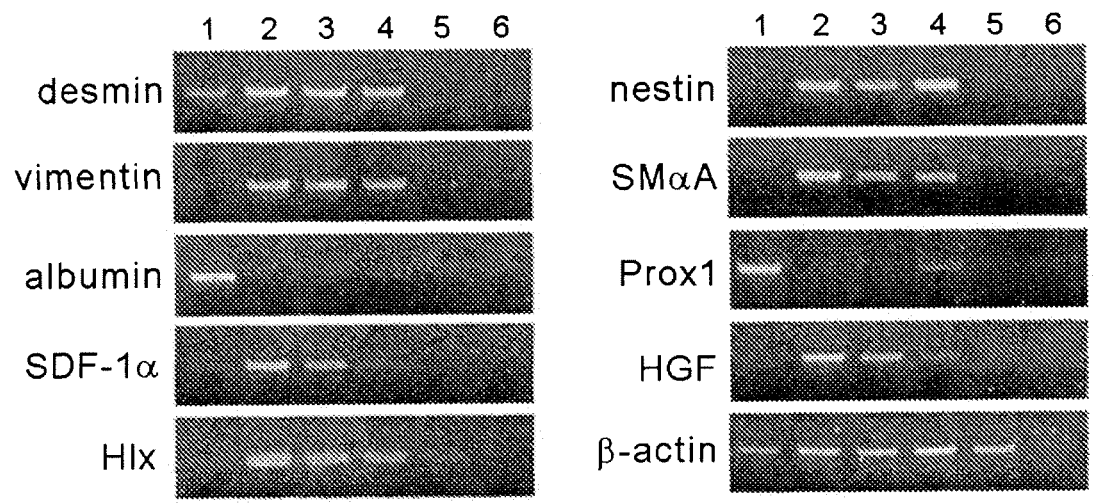
FIG. 5 provides RT-PCR analysis of 14 dpc fetal liver cells fractionated by FACS. Lane 1, ns-autoflu$^+$RT1A$^-$VCAM-1$^+$ β3-integrin$^-$; lane 2, vA$^+$RT1A$^-$VCAM-1$^+$β3-integrin$^+$; lane 3, autoflu$^-$RT1A$^-$VCAM-1$^+$; lane 4, autoflu$^-$RT1A$^-$VCAM-1$^-$; lane 5, remaining VCAM-1$^-$ cell population; lane 6, no cDNA. vA$^+$RT1A$^-$VCAM-1$^+$β3-integrin$^+$ cells express SDF-1α and HGF strongly. The vA$^+$ cells are positive for HpStC markers (desmin, nestin, vimentin, SMαA) and negative for hepatoblast markers (albumin and Prox1).

Interestingly, vA$^+$RT1A$^-$VCAM-1$^+$β3-integrin$^+$ cells expressed HGF, SDF-1α and H1x transcripts most strongly among all cell fractions examined (FIG. 5). Collectively, the vA$^+$RT1A$^-$VCAM-1$^+$β3-integrin$^+$ cells are desmin$^+$ nestin$^+$ SMαA$^+$ vimentin$^+$ H1x$^+$ and are main producers for HGF and SDF-1α in fetal liver.

Ex Vivo Clonal Expansion of RT1A$^-$VCAM-1$^+$β3-integrin$^+$ vA$^+$ Cells

Figure 6:
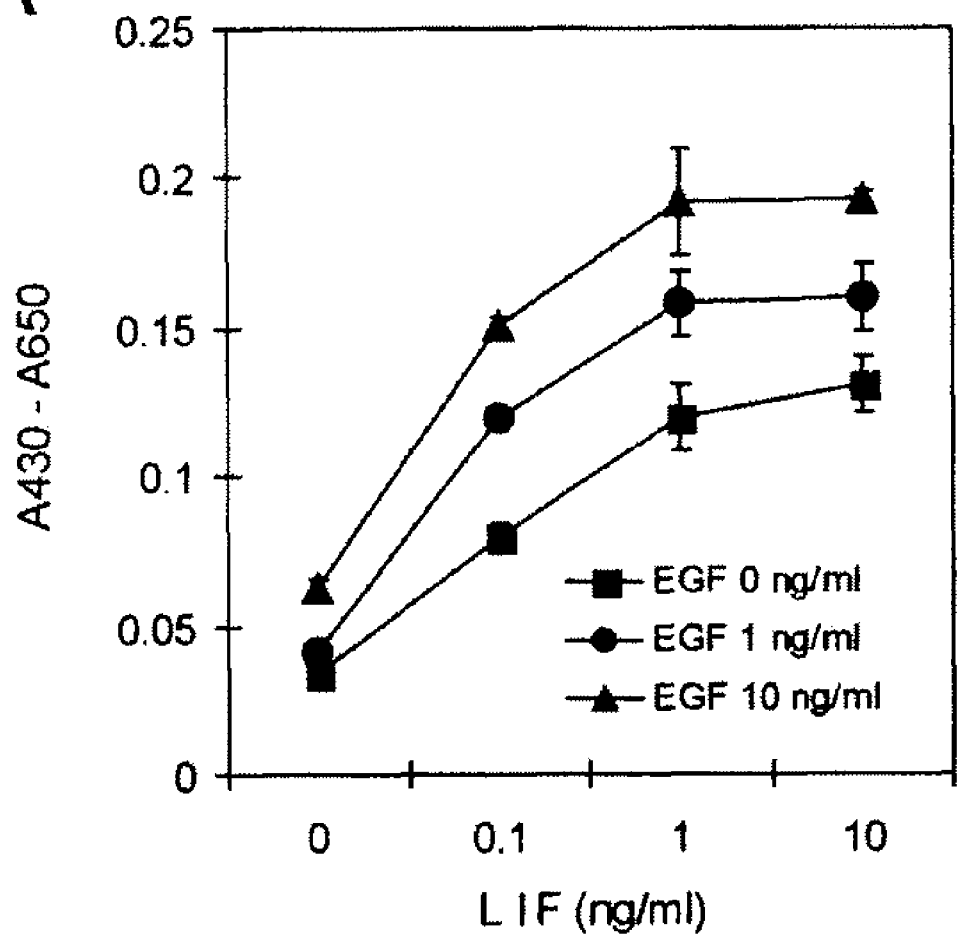
FIG. 6 shows the effect of LIF and EGF on in vitro proliferation of vA$^+$RT1A$^-$VCAM-1$^+$β3-integrin$^+$ cells. (A) Five hundred vA$^+$RT1A$^-$VCAM-1$^+$β3-integrin$^+$ cells isolated by FACS were placed in a well of 96-well plate with HDM plus laminin supplemented LIF and/or EGF at the concentration indicated. After 5 days-culture, degree of cell proliferation was measured by the tetrazolium salt WST-1. LIF support proliferation of the vA$^+$ cells at as low as 0.1 ng/ml. EGF slightly improved the vA$^+$ cell proliferation. (B) Two hundred fifty RT1A$^-$VCAM-1$^+$β3-integrin$^+$vA$^+$ cells isolated by FACS were seeded on STO feeder cells in HDM with EGF and/or LIF. Twelve-well plates were used. The cultures were stained with Diff-Quick™ after 2-week culture period. Although STO cells express LIF, the amount of the production was not adequate to support clonal expansion of the cells in the absence of exogenous LIF supplementation. Exogenous LIF and addition of EGF dramatically improved clonal expansion of the vA$^+$ cells.
Figure 6:
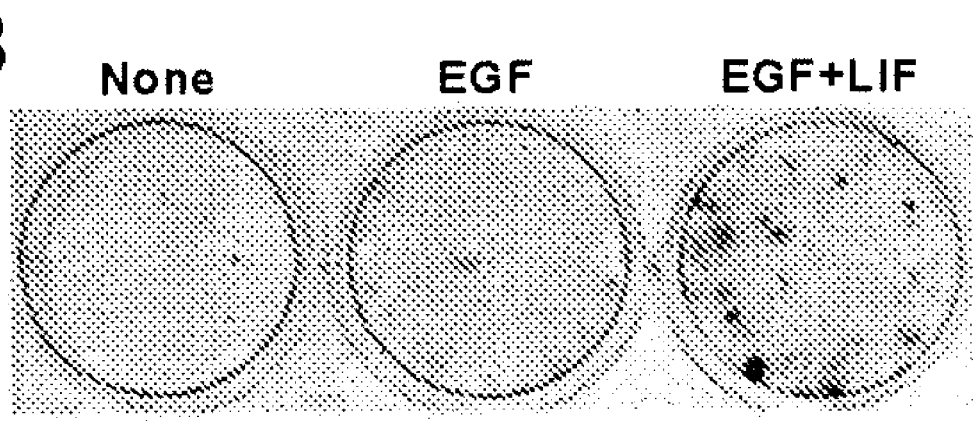

HpStCs isolated from adult liver have only limited proliferative activity in vitro. The ex vivo growth capability of the vA$^+$RT1A$^-$VCAM-1$^+$β3-integrin$^+$ cells in fetal livers was investigated, because HpStC precursors may have extensive proliferative activity. LIF is a pleiotrophic growth factor for many different types of cells including embryonic stem cells or myogenic cells. When vA$^+$RT1A$^-$VCAM-1$^+$β3-integrin$^+$ cells, which were isolated by FACS, were cultured with a hormonally defined serum-free medium at a cell density of 500 cells/well of 96 well-plates for 5 days in the presence of LIF, the cells expanded in a dose-dependent manner (FIG. 6A). In addition, EGF, a growth factor for various cell types including neural stem cells, enhanced the proliferation of HpStC precursors induced by LIF, but did not support the expansion on its own (FIG. 6A).

Figure 7:
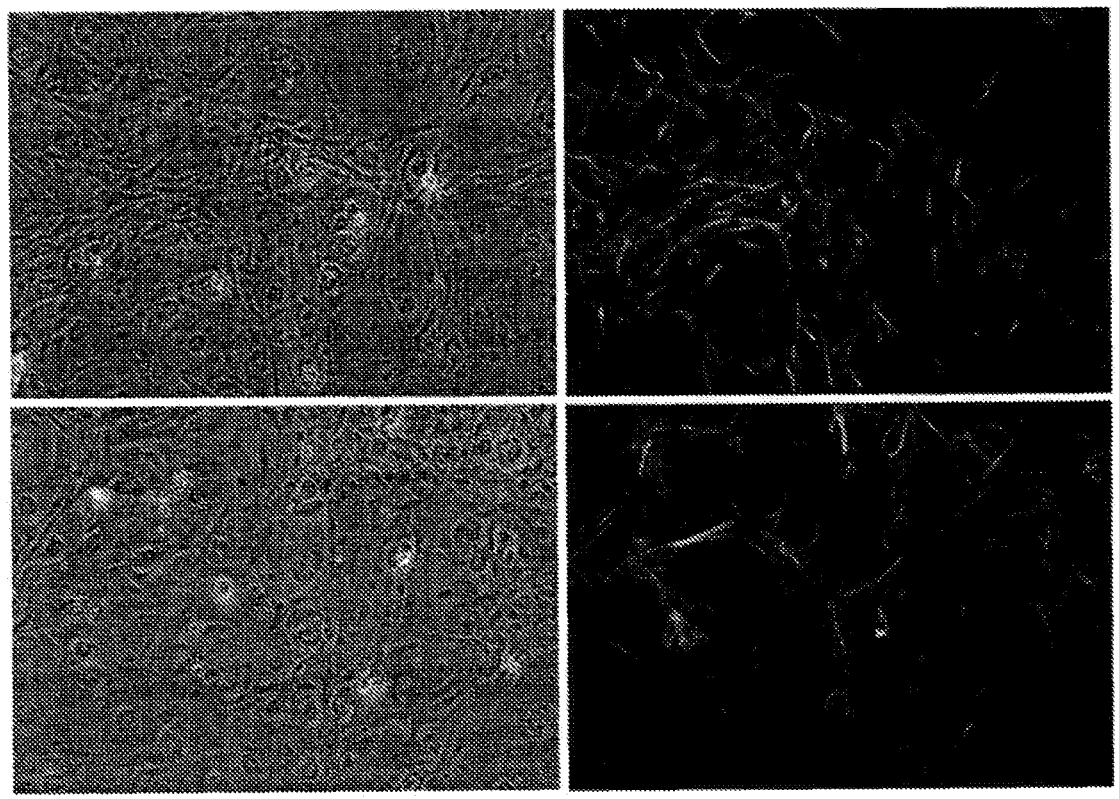
FIG. 7 shows the immunocytochemistry of colonies derived from vA$^+$RT1A$^-$ VCAM-1$^+$β3-integrin$^+$ cells isolated by FACS. Cells were placed on STO feeders in HDM supplemented with EGF and LIF. Fifteen days after in vitro culture, cultures were stained with antibodies for desmin or nestin. Colony forming cells express nestin and desmin, whereas STO cells do not express either.
Figure 8:
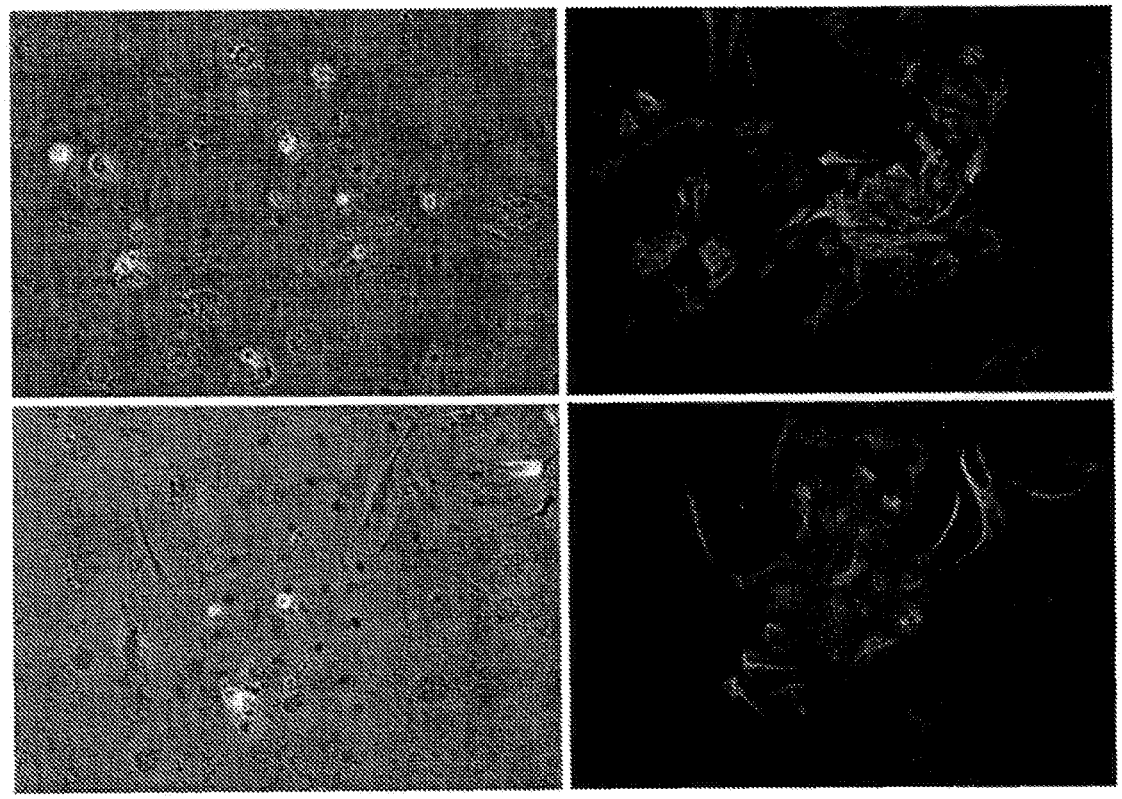
FIG. 8 shows the immunocytochemistry of 2-month cultured vA$^+$RT1A$^-$VCAM-1$^+$β3-integrin$^+$ cells isolated by FACS. Sorted cells were placed on STO feeders in HDM supplemented with EGF and LIF. Proliferating cells were subcultured 5 times on fresh STO feeders. Cultured cells were stained with antibodies for desmin or nestin. Proliferating cells maintain the expression of nestin and desmin during the culture period.

The proliferation, however, did not persist in the condition using plastic culture plates alone. Therefore, the FACS-sorted vA$^+$RT1A$^-$VCAM-1$^+$β3-integrin$^+$ cells were next placed on STO5 feeders (Kubota and Reid, 2000). Although LIF is produced by STO cells, exogenous LIF and supplementation of EGF further supported colony formation from sorted vA$^+$RT1A$^-$VCAM-1$^+$β3-integrin$^+$ cells dramatically (FIG. 6B). Proliferating cells in the culture expressed desmin and nestin, whereas STO5 feeders did not express either (FIG. 7). Three single colonies were picked and placed on fresh STO5 feeders. The single colony-derived cells continued to proliferate in the co-cultures with STO5 feeders supplemented with LIF and EGF for 2 months, indicating that they have extensive growth potential. Expression of desmin and nestin were maintained in the proliferating cells (FIG. 8).

To compare further the characteristic phenotypes of 2 month-cultured cells with freshly isolated vA$^+$RT1A$^-$VCAM-1$^+$β3-integrin$^+$ cells, RT-PCR was performed. Single colony-derived cells (A428-3) that were maintained for 2 months in culture were separated from STO5 feeder cells by FACS, and the RNA was extracted for RT-PCR analysis. RNA was isolated from STO5 feeder cells that were sorted simultaneously for a control sample. In addition, RNA was isolated from adult HpStCs to compare with those from A428-3 and STO5 cells.

Figure 9:
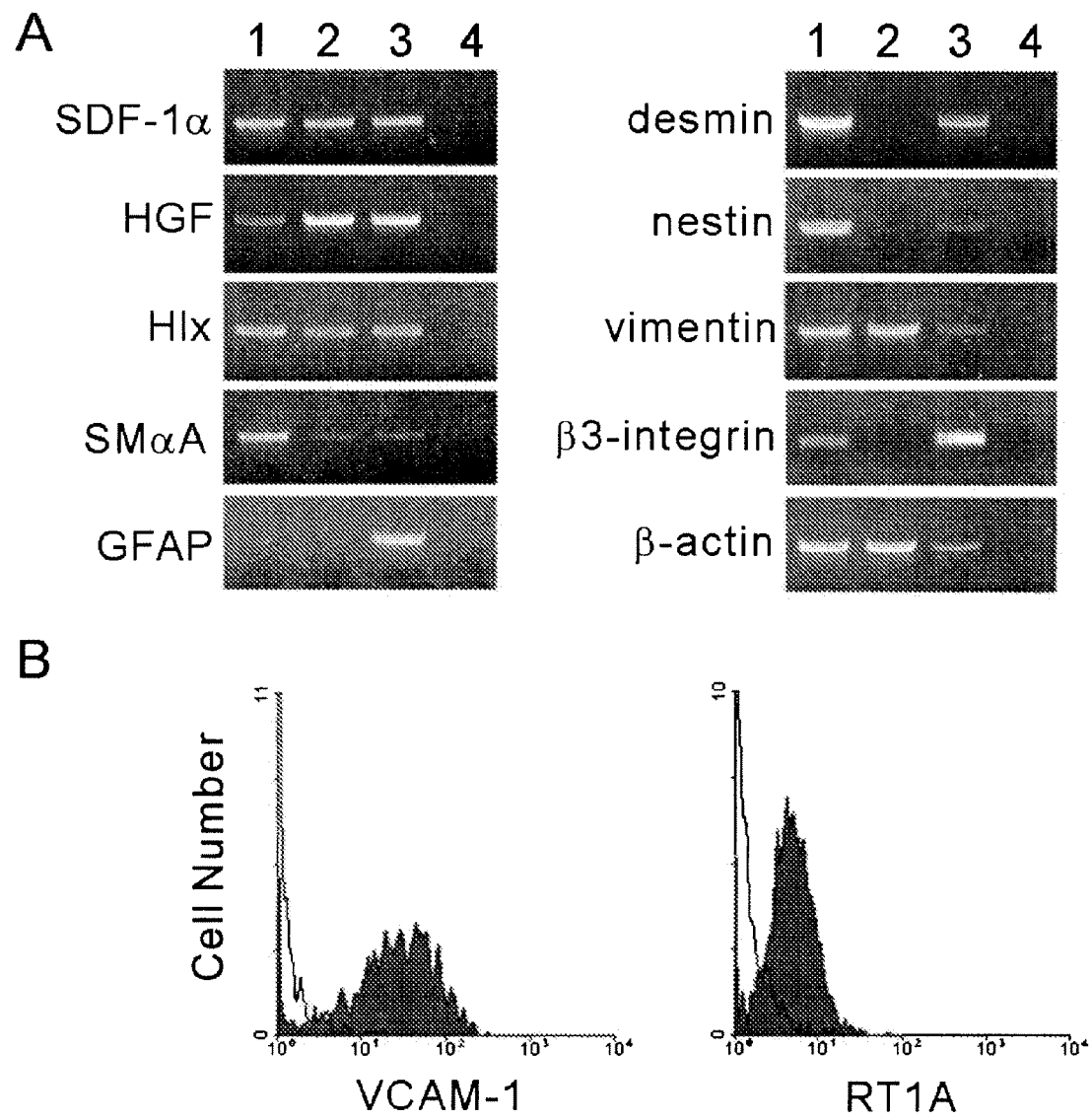
FIG. 9 provides phenotypic characteristics of 2-month cultured vA$^+$RT1A$^-$VCAM-1$^+$β3-integrin$^+$ cells. (A) RT-PCR analysis of cultured vA$^+$RT1A$^-$VCAM-1$^+$β3-integrin$^+$ cells. Cells were isolated by FACS and cultured on STO feeders in the HDM with EGF and LIF. After 2-month culture cells were fractionated by FACS. Proliferating rat cells and mouse STO feeder cells were fractionated by FACS following antibody staining of mouse CD98 monoclonal antibody. CD98 is expressed on mouse STO cells, and the monoclonal antibody reacts specifically mouse CD98, but not rat CD98. RNAs were isolated from vA$^+$-derived rat cells and STO cells. Normal rat HpStCs were also used and isolated the RNA for a control. cDNAs were synthesized from those RNAs and subjected to PCR with primers specific for various transcripts that expressed in HpStCs. (B) Flow cytometry for cultured vA$^+$RT1A$^-$VCAM-1$^+$β3-integrin$^+$ cells. Cells used for RT-PCR were stained with anti-VCAM-1 or RT1A antibody and mouse CD98 antibody. The CD98 negative fraction was analyzed for VCAM-1 or RT1A expression. Continuously proliferating cells derived from vA$^+$ cells in rat fetal livers express VCAM-1 and RT1A uniformly under the culture condition examined.

The results demonstrated that A428-3 expressed desmin, nestin, SMαA, vimentin, β3-integrin, SDF-1α, HGF, and H1x, indicating the expression pattern was a similar to fresh vA$^+$RT1A$^-$VCAM-1$^+$β3-integrin$^+$ cells (FIG. 5 and FIG. 9A). Furthermore, VCAM-1 expression was confirmed by FACS analysis (FIG. 9B). RT1A expression appeared to be induced in vitro culture (FIG. 9B). The RT-PCR results of adult HpStCs agreed with previous reports, in which the phenotype of normal adult HpStCs is desmin$^+$, glial fibrillary acidic protein (GFAP)$^+$, HGF$^+$, but SMαA$^{lo/-}$. The results also showed that adult HpStCs express SDF-1α, β3-integrin, and H1x. There was neither expression of GFAP in A428-3 cells (FIG. 9A) or in any fractions tested in fetal liver.

The present invention, however, provides additional markers that may be used in conjunction with the aforementioned markers to identify HpStC precursor cells, including, for example, β3-integrin+PECAM-1-VLA-6+ and CD44H–. ICAM-1 and β3-integrin are expressed on mature HpStCs as well. In addition to those surface markers, both mature and precursor HpStCs express intermediate filaments specific for HpStCs including desmin, vimentin, smooth muscle a-actin and nestin.

In this study, there was no detectable expression of GFAP in A428-3 cells (FIG. 9A) or in any fractions tested in fetal liver GFAP. Although GFAP is a marker used to identify astrocytes in central nervous system, the protein is also expressed in HpStCs in adult liver. However, we did not find GFAP mRNA by RT-PCR in any cell fractions examined as well as the whole fetal liver sample. In addition, even after culture of isolated HpStC precursors, GFAP expression was not induced, whereas desmin and nestin expression was sustained in the culture. This result suggests that HpStC precursors in fetal liver will acquire GFAP expression in a later developmental stage. We cannot, however, exclude another possibility, in which GFAP+ cells are derived from different precursors that do not exist in the 13 dpc fetal liver. Circulating cells in the blood flow may be a source of the alternative cellular origin. However, the majority of HpStCs in adult liver express GFAP; therefore, the minor contribution of circulating cells from the blood are unlikely to become a dominant population in the liver. Thus, it seems more likely that acquisition of GFAP expression happens during maturation of HpStCs.

The data also indicated that HpStC precursors expressed the divergent homeobox protein, H1x, relatively strongly. Although the relationship between H1x expression and HpStC development is not clear, loss of H1x expression may contribute to the defects in the mutant mice. HpStC precursors in the mouse fetal liver express HGF, SDF-1α and H1x as well.

In addition to the unique surface phenotype of HpStC precursors, the culture system established in this study can be use to identify HpStC precursors in adult liver. Until now, HpStCs from adult liver have been cultured in medium supplemented with fetal bovine serum. Normally, HpStCs cultured in the serum-supplemented medium give rise to myofibroblastic cells, which acquired fibroblastic characteristics and lose the original HpStC phenotypes. Therefore, the serum-supplemented medium conditions are not appropriate to identify HpStC precursors. The serum-free culture conditions described in this study support ex vivo maintenance of HpStC progenitors.

It seems that HpStC precursors plays key roles for liver development, because they express more HGF transcript than any subpopulation in fetal liver cell fractions examined. HGF is a crucial growth factor for hepatic development (Schmidt et al., 1995), and the factor is responsible for liver parenchymal cell growth during liver regeneration as well (Michalopoulos and DeFrances, 1997). In addition, it has been shown that HpStCs, but not parenchymal cells, endothelial cells, or Kupffer cells, are the producer for HGF in adult liver (Schirmacher et al., 1992). Therefore, our data and that from previous studies suggest that HpStCs are the main HGF producers from fetuses to adults in the liver.

In this study, there was no GFAP expression in 13 dpc fetal liver. Although GFAP is a marker used to identify astrocytes in central nervous system, the protein is also expressed in HpStCs in adult liver. However, we did not find GFAP mRNA by RT-PCR in any cell fractions examined as well as the whole fetal liver sample. In addition, even after culture of isolated HpStC precursors, GFAP expression was not induced, whereas desmin and nestin expression was sustained in the culture. This result suggests that HpStC precursors in fetal liver will acquire GFAP expression in a later developmental stage. We cannot, however, exclude another possibility, in which GFAP+ cells are derived from different precursors that do not exist in the 13 dpc fetal liver. Circulating cells in the blood flow may be a source of the alternative cellular origin. However, the majority of HpStCs in adult liver express GFAP; therefore, the minor contribution of circulating cells from the blood are unlikely to become a dominant population in the liver. Thus, it seems more likely that acquisition of GFAP expression happens during maturation of HpStCs.

A divergent homeobox protein, H1x, is expressed in the septum transversum and mesenchymal cells in fetal liver (Lints et al., 1996). A previous study of H1x knockout mice demonstrated that the mutant mice have impaired hepatic development and fetal liver hematopoiesis (Hentsch et al., 1996).

Transplantation experiments indicated that the hematopoietic defect was caused by the fetal liver microenvironment, but not by the hematopoietic progenitors per se. Thus, H1x+ cells are a crucial cell population in fetal liver for supporting hepatic and hematopoietic development. Our data indicated that HpStC precursors expressed H1x strongly. Therefore, it is interesting to examine whether H1x knockout mice have HpStC precursors. Although the relationship between H1x expression and HpStC development is not clear, loss of H1x expression may contribute the defects in the mutant mice. Recently, we found that similar HpStC precursors in the mouse fetal liver expressed HGF, SDF-1a, and H1x as well. Further, the present inventors have identified mesenchymal cells with similar markers (e.g., smooth muscle alpha-actin) in human fetal livers and that have proven vital for the ex vivo expansion of human hepatic stem cells.

HpStC precursors that were purified by FACS proliferated on STO feeders and under serum-free media conditions supplemented with lipids, insulin, transferrin, EGF and LIF. Our data indicated LIF is more beneficial for in vitro proliferation. With the support of STO feeders, HpStC precursors replicated continuously for more than 2 months. Cultured cells expressed VCAM-1, β-3-integrin, desmin, vimentin, smooth muscle alpha-actin, nestin, HGF and SDF-1a. These phenotypes of fresh HpStC precursors did not change during in vitro culture.

In addition to the unique surface phenotype of HpStC precursors, the culture system established in this study can be use to identify HpStC precursors in adult liver. Until now, HpStCs from adult liver have been cultured in medium supplemented with fetal bovine serum. Normally, HpStCs cultured in the serum-supplemented medium give rise to myofibroblastic cells, which acquired fibroblastic characteristics and lose the original HpStC phenotypes. Therefore, the serum-supplemented medium conditions are not appropriate to identify HpStC precursors. The serum-free culture conditions described in this study support ex vivo maintenance of HpStC progenitors. If there exist HpStC precursors in adult liver, they would be a valuable resource to replace activated HpStCs in fibrogenic liver. Phenotypic identification and an in vitro culture system for HpStC precursors will facilitate the development of novel therapeutic approaches for liver diseases.

While the invention has been described in connection with specific embodiments thereof, it will be understood that it is capable of further modifications and this application is intended to cover any variations, uses, or alterations of the invention following. In general, the principles of the invention and including such departures from the present disclosure as come within known or customary practice within the art to which the invention pertains and as may be applied to the essential features hereinbefore set forth and as follows in the scope of the appended claims.

We claim:

1. A method of obtaining a population of cells enriched in hepatic stellate cell progenitors comprising:
   (a) providing a single cell suspension of cells from mammalian fetal liver tissue; and
   (b) sequentially, in any order, or substantially simultaneously,
      (i) removing from the single cell suspension those cells that express MHC class Ia antigen and glial fibrillary acidic protein (GFAP); and
      (ii) isolating from the cell suspension those cells that are positive for Vitamin A fluorescence,
   to obtain a population of cells enriched in hepatic stellate cell progenitors.

2. The method of claim 1, wherein step (b) further comprises: (iii) isolating those cells that are positive for VCAM.

3. The method of claim 1, wherein step (b) further comprises: (iii) removal of those cells expressing CD45.

4. The method of claim 1, wherein step (b) further comprises: (iii) isolating those cells that are positive for both VCAM and β3-integrin.

5. The method of claim 1, further comprising: (iii) isolating from the cell suspension those cells that express desmin, nestin, vimentin, smooth muscle alpha-actin or a combination thereof.

6. The method of claim 1 in which the isolating and removing steps are carried out using flow cytometry.

7. The method of claim 1 in which the hepatic stellate cell progenitors are human hepatic stellate cell progenitors.

8. A method of obtaining a population of cells enriched in hepatic stellate cell progenitors comprising:
   (a) obtaining a cell suspension of fetal liver cells; and
   (b) sequentially, in any order, or substantially simultaneously,
      (i) isolating from the cell suspension of liver cells those cells that are positive for ICAM antigen,
      (ii) removing from the cell suspension those cells that are positive for MHC class I antigen and glial fibrillary acidic protein (GFAP), and
      (iii) isolating from the cell suspension those cells that are positive for Vitamin A fluorescence as measured in a flow cytometer,
   to obtain a population of cells enriched in hepatic stellate cell progenitors.

9. The method of claim 8, wherein step (b) further comprises: (iv) isolating from the cell suspension those cells that express desmin, nestin, vimentin, smooth muscle alpha actin or a combination thereof.

10. The method of claim 8 in which the isolating and removing steps are carried out in a flow cytometer.

11. The method of claim 8 in which the removal of those cells that express MHC class I antigen is carried out with an antibody.

12. The method of claim 8 in which the hepatic stellate cell progenitors are human hepatic stellate cell progenitors.

\* \* \* \* \*